United States Patent
O'Connor

(10) Patent No.: US 9,060,732 B2
(45) Date of Patent: Jun. 23, 2015

(54) MULTI-SEGMENT SLANT HOLE COLLIMATOR SYSTEM AND METHOD FOR TUMOR ANALYSIS IN RADIOTRACER-GUIDED BIOPSY

(71) Applicant: MAYO Foundation for Medical Education and Research, Rochester, MN (US)

(72) Inventor: Michael K. O'Connor, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/715,217

(22) Filed: Dec. 14, 2012

(65) Prior Publication Data

US 2013/0158389 A1    Jun. 20, 2013

Related U.S. Application Data

(60) Provisional application No. 61/576,746, filed on Dec. 16, 2011.

(51) Int. Cl.
*A61B 6/00* (2006.01)
*A61B 8/00* (2006.01)
(Continued)

(52) U.S. Cl.
CPC ............... *A61B 6/4258* (2013.01); *A61B 8/00* (2013.01); *A61B 10/0266* (2013.01); *A61B 6/502* (2013.01); *A61B 8/0825* (2013.01); *A61B 8/403* (2013.01); *A61B 8/4411* (2013.01); *A61B 8/4416* (2013.01); *A61B 8/485* (2013.01); *A61B 6/4291* (2013.01); *A61B 6/4417* (2013.01);
(Continued)

(58) Field of Classification Search
CPC .... A61B 6/4258; A61B 8/00; A61B 10/0266; A61B 6/502; A61B 8/0825; A61B 8/403; A61B 8/4411; A61B 8/4416; A61B 8/485; A61B 8/4291; A61B 8/4417; A61B 10/0233; A61B 2017/3411; A61B 2019/205; A61B 2019/507; G01T 1/2985
USPC .................................................. 600/407–436
See application file for complete search history.

(56) References Cited

U.S. PATENT DOCUMENTS 3,777,148 A    12/1973  Miraldi
4,079,259 A    3/1978  Blum
(Continued)

FOREIGN PATENT DOCUMENTS

WO    2010077626    7/2010
WO    2010120525    10/2010

*Primary Examiner* — Sanjay Cattungal
(74) *Attorney, Agent, or Firm* — Yakov Sidorin; Quarles & Brady LLP

(57) ABSTRACT

A system and method for molecular breast imaging (MBI) provides enhanced tumor analysis and, optionally, a real-time biopsy guidance. The system includes a detector head including a gamma ray detector and a multisegment collimator in a collimator frame. The collimator contains multiple collimation sections that have respectively different collimating characteristic and that are individually repositionable with respect to the detector. An image of the tissue acquired with the system may include spatially separate image portions containing image information about the same portion of the imaged tissue. A system of mounting the multisegment collimator in the detector head includes a collimator tray that is laterally moveable within the frame and/or slidable in and out of the frame.

18 Claims, 13 Drawing Sheets

(51) Int. Cl.
    *A61B 10/02*    (2006.01)
    *A61B 8/08*     (2006.01)
    *G01T 1/29*     (2006.01)
    *A61B 17/34*    (2006.01)
    *A61B 19/00*    (2006.01)

(52) U.S. Cl.
    CPC ..... *A61B10/0233* (2013.01); *A61B 2017/3411* (2013.01); *A61B 2019/205* (2013.01); *A61B 2019/507* (2013.01); *G01T 1/2985* (2013.01)

(56) References Cited

U.S. PATENT DOCUMENTS

| | | |
|---|---|---|
| 4,181,839 A | 1/1980 | Hatton |
| 4,419,585 A | 12/1983 | Strauss et al. |
| 4,792,686 A | 12/1988 | Karcher et al. |
| 6,424,693 B1* | 7/2002 | Weisenberger ............... 378/37 |
| 6,583,420 B1* | 6/2003 | Nelson et al. ................. 250/397 |
| 7,230,246 B2 | 6/2007 | Hawman |
| 7,291,841 B2* | 11/2007 | Nelson et al. ............ 250/370.09 |
| 2002/0143249 A1* | 10/2002 | Tornai et al. .................. 600/425 |
| 2003/0205676 A1* | 11/2003 | Nelson et al. ............ 250/370.09 |
| 2003/0209672 A1* | 11/2003 | Nelson et al. ................. 250/394 |
| 2004/0251419 A1* | 12/2004 | Nelson et al. ............ 250/370.09 |
| 2010/0016865 A1* | 1/2010 | Kieper et al. ................. 606/130 |
| 2010/0261997 A1* | 10/2010 | Ren et al. ...................... 600/424 |
| 2011/0158384 A1* | 6/2011 | Beekman ........................ 378/37 |
| 2012/0130234 A1* | 5/2012 | O'Connor et al. ........... 600/427 |
| 2014/0093035 A1* | 4/2014 | Beekman ........................ 378/37 |

* cited by examiner

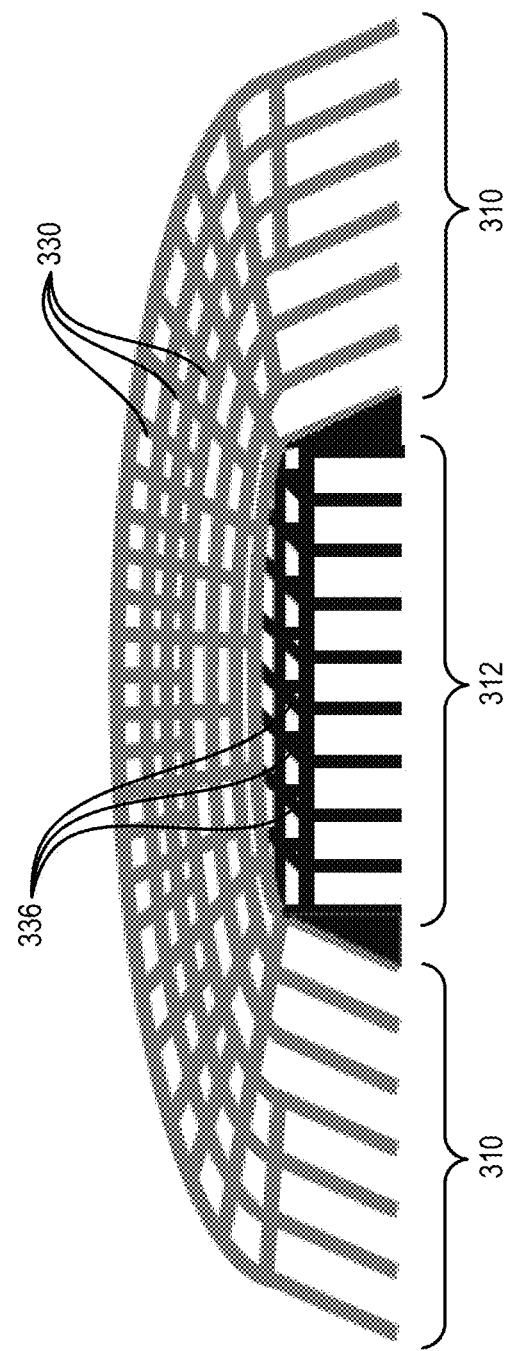

MULTI-SEGMENT SLANT HOLE COLLIMATOR SYSTEM AND METHOD FOR TUMOR ANALYSIS IN RADIOTRACER-GUIDED BIOPSY

CROSS-REFERENCE TO RELATED APPLICATIONS

The present application claims priority from and benefit of the U.S. Provisional Patent Application Ser. No. 61/576,746 filed on Dec. 16, 2011 and titled "Multi-Segment Slant Hole Collimator System and Method For Tumor Analysis in Radiotracer-Guided Biopsy". The entire disclosure of the abovementioned provisional application is incorporated by reference herein for all purposes.

STATEMENT REGARDING FEDERALLY SPONSORED RESEARCH

This invention was made with government support under Grant No. NCI R44 CA 143716, awarded by the National Institute of Health. The government has certain rights in the invention.

TECHNICAL FIELD

The present invention relates to systems and methods for imaging and, more particularly, to systems and methods for tumor location analysis and real-time biopsy guidance using radiotracing.

BACKGROUND OF THE INVENTION

Breast cancer screening has been recommended for many decades, particularly for women over the age of fifty. The combination of early detection and improved therapy of breast cancer in the U.S. has resulted in a significant reduction in breast cancer mortality, with similar reductions being observed in other countries. Despite the success of screening mammography, however, it is also recognized that mammography is a less than perfect screening method. The limitations of mammography are particularly evident when it is used on women having mammographically-dense breasts. It has been shown that the sensitivity of mammography decreases with increasing mammographic density, and is less than fifty percent for women with an extremely dense breast pattern on a mammogram.

The reduction of sensitivity of mammography with the increase of mammographic density is compounded by the fact that increased breast density is a significant risk factor for breast cancer. Given that a dense breast pattern is more characteristic of younger women, this factor significantly diminishes the value of mammography in the screening of young women who have a high familial or genetic risk of breast cancer.

A second major limitation to screening mammography lies in the evaluation of women at high risk of breast cancer. Numerous studies have demonstrated that, when performed on women with a high genetic risk of breast cancer, mammography has a sensitivity of between about 33 and about 43 percent. Most of these studies have been performed with women with an average age of forty, so part of the explanation for the poor performance of mammography in these studies may be due to the presence of dense breast patterns in a significant percentage of the mammographic images.

A possible solution to the problem of the detection of breast lesions in dense breast tissue is to use ultrasound-based techniques with such patients. Ultrasound (US) techniques are attractive for supplemental screening because they are widely available, well-tolerated by patients, and involve no exposure of the patients to radiation. However, while supplemental US screening uncovers more occurrences of breast cancer, it also substantially increases the risk of a "false positive" cancer finding and unnecessary biopsy. Hence, the use of whole-breast ultrasound as a sole identifier of breast malignancies is questionable. Even in combination with mammography, the two anatomical techniques have significant limitations. It would be of considerable benefit to provide another complementary method that offers functional information about lesions available from the results of the US screening. Such a method would significantly reduce the number of "false positive" cases, and allow the radiologist to evaluate those lesions that demonstrate both a functional and anatomical abnormality.

Over the last five years, several nuclear medicine-based technologies have been developed that have application in breast imaging. Included in these are positron emission mammography ("PEM") and molecular breast imaging ("MBI"). In PEM the breast is compressed between two opposing detectors and the 511 keV gamma rays emitted by a positron-emitting radiopharmaceutical, such as F-18 fluoro-deoxyglucose, for example, are detected by coincidence imaging between the two opposing detectors. The PEM images provide an image of glucose utilization by breast tissue and have been shown to be capable of detecting small cancers in the breast. Unlike anatomical techniques such as mammography and ultrasound, PEM is not influenced by dense breast tissue.

The second nuclear medicine-based technique is MBI. This technology employs one or two small gamma cameras. The breast is compressed between a camera and a compression paddle, or between two gamma cameras, and radiation emitted by a single-photon radiopharmaceuticals, such as Tc-99m sestamibi, is detected after collimation. MBI is a planar imaging technique without tomographic capability; however, information from two opposing gamma cameras can be used to calculate the true depth of a functional abnormality in the MBI images. The MBI system has been shown to have a very high sensitivity (for example in some cases greater than ninety percent) for the detection of lesions smaller than ten millimeters across. In addition, it has been found that, in some cases, MBI can detect three times as many cancer occurrences as digital and analog mammography in asymptomatic women at increased risk of breast cancer.

Beyond sensitivity differences, technologies that provide functional images of the breast tissue, such as MBI, can detect lesions not visible with conventional mammography. Likewise, in some cases it may not be practical to co-register and co-analyze anatomical images from one imaging modality, such as ultrasound systems, and functional images from MBI to further facilitate guided biopsies. For example, one might desire to use anatomical images gathered in substantially real time from an ultrasound imaging system to aid in biopsy guidance coupled with MBI images. However, the logistics of such a process would be quite difficult. For example, US imaging typically requires that the patient be supine and that a handheld scanner be used to scan the breast tissue. In comparison, MBI is usually performed with the patient seated and the breast lightly compressed between the gamma cameras or a camera and paddle. MBI employs light compression forces, for example 10-15 pounds of force, with imaging times in the 5-10 minute range. Because of the differences in patient orientation alone between MBI and ultrasound, the shapes of the breast tissue being imaged with the use of these two modalities are significantly different and, hence, the correlation of an anatomical abnormality with a functional abnormality becomes complicated. Therefore, accurate co-registration of anatomical images from ultrasound and functional information from MBI is not currently possible.

It would therefore be desirable to provide a system and method that provides functional images of the breast and enables real-time feedback of interventional procedures.

SUMMARY OF THE INVENTION

The present invention provide a molecular breast imaging (MBI) system that include a detector head containing a collimator frame, a first collimator within the collimator frame, and a first gamma-ray detector configured to receive gamma-rays from a portion of a subject arranged proximate to the first collimator. The first collimator contains multiple collimating sections that are independently repositionable with respect to the collimator frame and that have different collimation characteristics such as, for example, different collimation angles. In a specific configuration, the multiple collimating sections include four collimating sections and different collimation characteristics include different foci respectively corresponding to different collimating sections.

In one configuration, the first collimator is disposed in a tray adapted to repositionably fit within the collimator frame. In a specific arrangement, such tray is moveable within the bounds of the collimator frame and, in addition or alternatively, slidable in and out of the collimator frame. The multiple collimating sections include at least one collimating section that is orientable at discrete predetermined angles within the tray.

In a related configuration, the above mentioned MBI system additionally includes a second detector head containing a second collimator and a second gamma-ray detector that is configured to receive gamma-rays from the portion of the subject arranged between the first collimator and the second collimator. The multiple collimating sections of the first collimator may include a collimating section with linearly configured slant-holes that are inclined with respect to a normal to a surface of such collimating section. The second collimator may contain slant-holes that are substantially parallel to an axis that is normal to a surface of the second collimator. In a specific implementation, the second detector head is configured to be removably engaged with the MBI system and optionally substituted with an acoustic coupling element (configured to engage with the MBI system to receive an ultrasound imaging apparatus) or a biopsy element (configured to engage with the MBI system to receive and pass a biopsy needle through the biopsy element toward the first detector head). An arrangement of the system may further include a gantry system supporting the first and second detector heads to permit relative motion of the first and second detector heads about the gantry system.

The invention additionally provides an MBI system that includes an upper compression pad and a lower compression pad. The lower compression pad is associated with a gamma-ray detector and a collimator configured to deliver gamma-rays from a region of interest (ROI) of the breast tissue in a gamma-ray pattern that includes first and second spatially-separate pattern regions. Particularly, the collimator includes multiple collimating sections that are individually repositionable with respect to the upper compression pad. The lower compression pad further includes a collimator sleeve, and the collimator contain a first collimating section having a first collimation angle and a second collimating section having a second collimation angle. These collimating sections are cooperated to be re-orientable and/or re-positionable with respect to the collimator sleeve.

The invention additionally provides a method for performing an image-guided biopsy of a tissue. Such method includes a step of (i) positioning a portion of the tissue to be imaged between first and second compression members. One of the compression members includes a gamma-ray detector in operable communication with a collimator that contains multiple individually repositionable collimation sections having different collimation characteristics. The method additionally includes steps of (ii) initiating a biopsy procedure on the portion of tissue through one of the compression members; (iii) displaying an image of the portion of the tissue based on information acquired by the gamma-ray detector about gamma rays that have passed through the multiple collimation sections; and (iv) processing imaging data representing a status of the biopsy procedure. In one configuration, the step of displaying an image may include displaying an image that represents a common, substantially spatially-overlapping area in the portion of the tissue that is spatially displaced in the image. Alternatively or in addition, the step of positioning may include positioning a portion of the tissue being imaged in proximity to a compression member that is configured to receive a re-attachable device. The step of processing imaging data may include processing imaging data representing a location of a biopsy needle with respect to at least one of the first and second compression members.

A method may additionally include a step of (v) receiving ultrasound imaging data from an acoustic coupling element coordinated with the second compression member opposite the collimator. Furthermore, a method may contain a step of determining parameters of spatial location of a biopsy needle within the tissue, which parameters include a depth value derived from geometry of said displayed image.

BRIEF DESCRIPTION OF THE DRAWINGS

The invention will be more fully understood by referring to the following Detailed Description of Specific Embodiments in conjunction with the Drawings, of which:

FIG. 4A is a perspective, partial cross-sectional view of a conical slant-hole collimator of FIG. 3.

DETAILED DESCRIPTION

Figure 1:
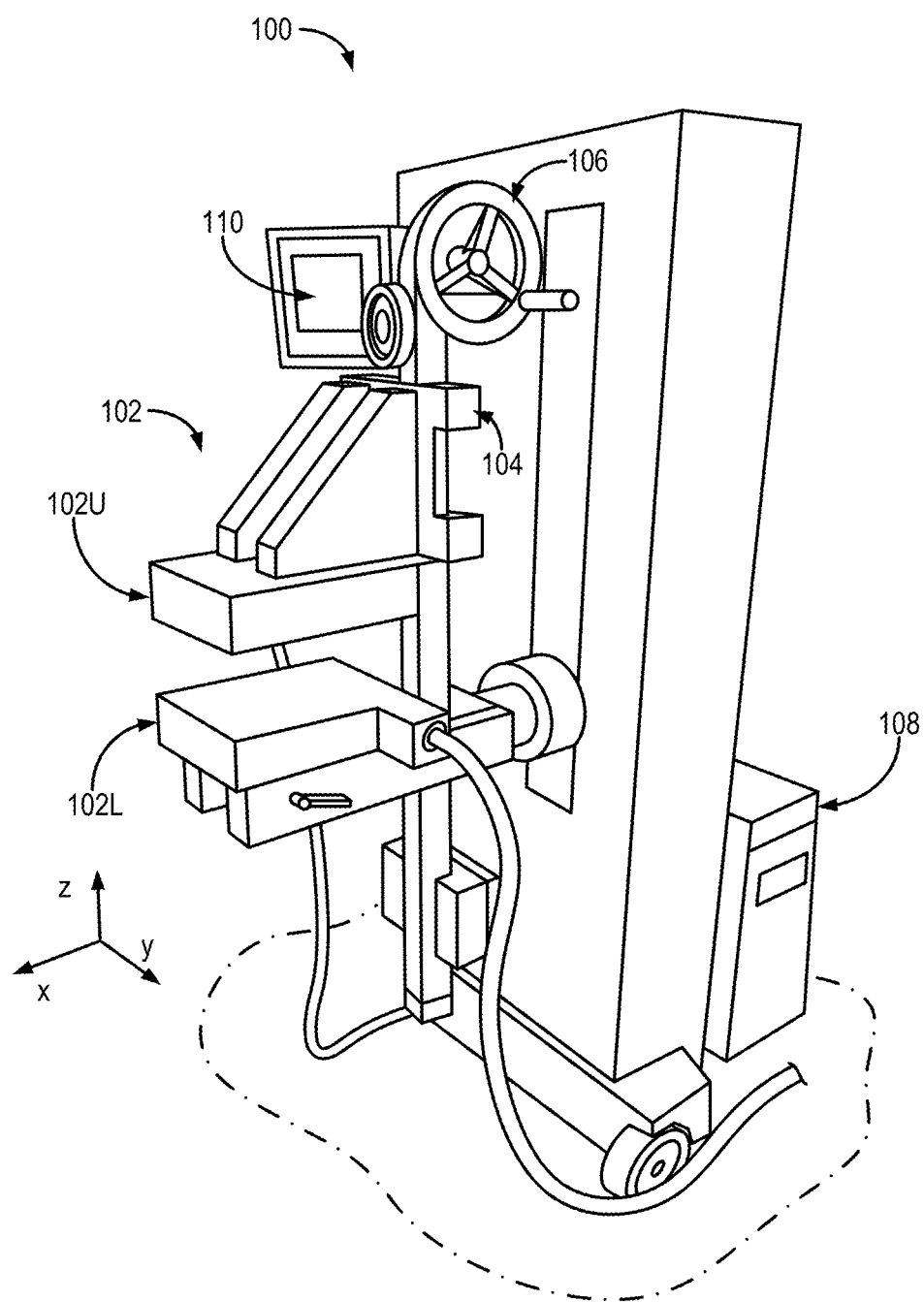
FIG. 1 is an illustration of a molecular breast imaging ("MBI") system according to the present invention.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in claims appended to this disclosure is intended to be assessed in light of the disclosure as a whole.

Referring now to FIG. 1, an embodiment of a molecular breast imaging ("MBI") system 100 includes two opposing detector heads 102 containing cadmium zinc telluride ("CZT") detectors. In particular, the detector heads (or detector head assemblies) 102 include an upper detector head 102U and a lower detector head 102L. Examples of MBI systems and methods for their use are described, for example, in a co-pending U.S. patent application Ser. No. 12/515,369, the disclosure of which is herein incorporated by reference in its entirety. Each detector head 102U, 102L is sized to be, for example, 20 centimeters ("cm") by 16 cm (or has a similar size) and mounted on a modified upright type mammographic gantry 104. In one configuration, the detector heads 102 include Lumagem® 3200S high-performance, solid-state cameras from Gamma Medica-Ideas, Inc., having a pixel size of 1.6 millimeters ("mm") (Lumagem® is a trademark of Gamma Medica-Ideas, Inc., Northridge, Calif.).

The relative position of the detector heads 102 can be adjusted using a user control 106. In a related embodiment (not shown), the positioning of the detector heads 102 is controlled with a computer processor. In a specific embodiment, the detector head assemblies 102 are configured to operate as a compression mechanism that squeezes or compresses a breast of a subject between the head assemblies 102U and 102L. Accordingly, this system configuration reduces the maximum distance between any lesion in the breast and either detector head 102U, 102L to about one-half or less of the total breast thickness, thereby potentially increasing the probability and efficiency of the detection of small lesions without additional imaging time or dose. The MBI system 100 includes a processor 108 that is programmable to process the signals and/or imaging data acquired by the detector heads 102 to produce an image, which may be displayed on an associated display 110.

Figure 2:
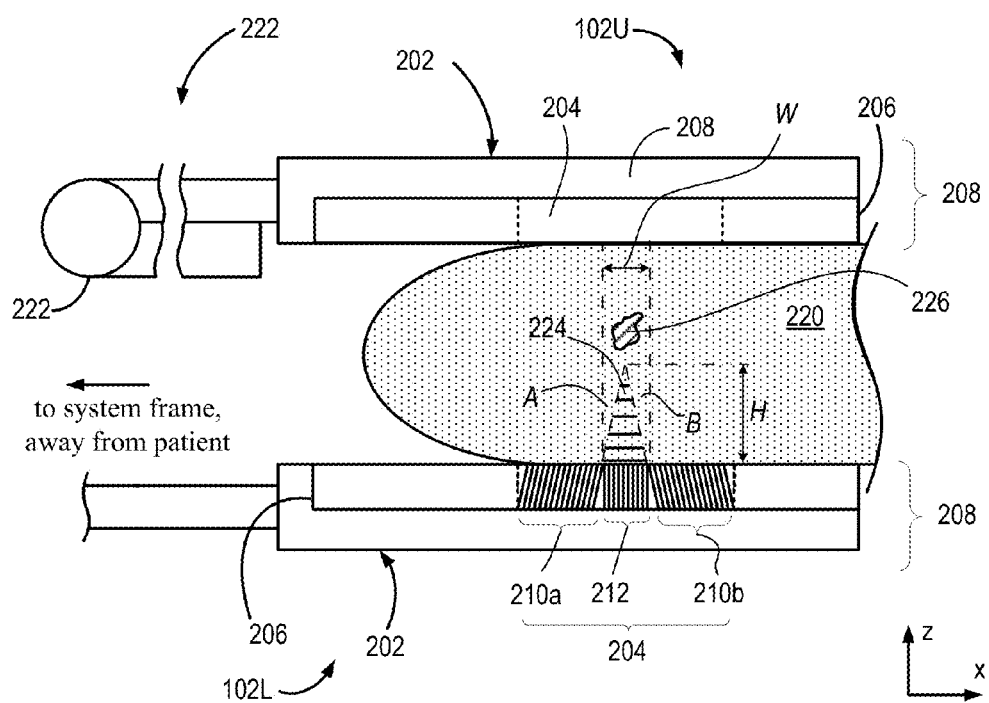
FIG. 2 is a side elevational illustration of the pair of opposed gamma detector heads of FIG. 1 showing a cross-sectional view of a slant-hole collimator having a 2D-varying structure.

Referring to FIG. 2, a two-dimensionally (2D) varying embodiment of the collimator is described. As shown, each of the heads 102L, 102U is not to scale and may include a corresponding gamma-ray detector 202 and an embodiment of the corresponding 2D slant-hole collimator 204 positioned in a corresponding collimator frame 206 next to the corresponding gamma-ray detector 202. While FIG. 2 shows structural details of only the collimator 204 of the lower detector head 102L, the structure of the collimator 204 of the upper detector head 102U (should the head 102U include the collimator) is similar and is not shown here for simplicity of illustration. The collimator frame 206 is appropriately sized to be received by a recessed portion of the detector head 202. The inner extent of the collimator frame 206 is adapted to receive and accommodate the collimator 204 therein, such that the collimator 204 is positioned in spatial alignment with a detector array 208 (such as, for example, a cadmium zinc telluride or CZT detector array) formed in cooperation with a surface of the detector-head 202.

As shown in FIG. 2, the collimator 204 contains three separate collimating sections, 210a, 210b, and 212. The holes or channels of the first and second sections 210a, 210b of the collimator 204 are slanted or inclined with respect to the breast 220, at corresponding angles A and B (not shown) from lateral to medial and vice versa. At the same time, within the corresponding region 210a or 210b, the holes of channels are mutually parallel, from chest wall to nipple. In one embodiment, the measures of angular inclination (and corresponding collimation angles of sections 210a, 210b) A, B may be opposite in signs but equal in absolute value. Generally, as measured with respect to the normal to the gamma-ray collecting surface of the collimator 204, the angles A, B are acute (in one embodiment, for example, 30 degrees) or, as measured with respect to the gamma-ray collecting plane of the collimator 204, obtuse. Similarly, the holes or channels of the third section 212 extend vertically (i.e., normally with respect to the gamma-ray collecting surface of the collimator 204) across the breast 220 from lateral to medial and vice versa and, at the same time, are mutually parallel across whole the region 212 from chest wall to nipple. The collimating section 212, therefore, is characterized by a collimation angle of substantially 90 degrees as measure with respect to the gamma-ray collecting plane of the collimator 204. The structure of the collimator 204 has, therefore, a 2D-varying geometry: the structure of either of the sections 210a or 210b with section 212 of the collimator 204 remains the same as viewed in any cross-sectional plane that is parallel to the xz-plane of FIG. 2, and remains substantially unchanged along the y-axis of FIG. 2.

In comparison with a traditional collimator that contains a single collimating section, the holes or channels of which are directed substantially perpendicular to the plane of a supporting detector head (for example, to the plane of the head 102L or xy-plane), the embodiment 204 is characterized by an approximately two-fold increased sensitivity and, in addition, permits estimation of the depth of the lesion 226 within the breast tissue 220. As discussed further below, the assessment of lesion depth in the breast 220 is effectuated by considering the relative distances to the lesion as reflected by portions of the image that are respectively associated with the collimating sections 210a, 210b, and 212 of the collimator 204.

Specifically, and in further reference to FIG. 2, the three-sectional structure of the collimator 204 defines a "dead" or "dark" zone denoted in a cross-sectional view of FIG. 2 as a triangular area 224. The terms "dead" or "dark" refer to the fact that the zone 224, while visible by central collimating portion 212, is not visible by the peripheral collimating portions 210a, 210b. More particularly, the zone 224 is defined above the central collimating portion 212 and is bounded by the planes containing, respectively, the holes or channels of the sections 210a, 210 that are closest to the section 212. It is appreciated that a portion of the breast tissue 220 that is located substantially within the bounds of the zone 224 is imaged through the central collimating section 212 but is not imaged through the collimating sections 210a, 210b containing the slanted holes or channels. Indeed, imaging gamma rays that propagate through the breast 220 from the upper detector-head 102U downwards, in a -z direction towards the detector-head 102L and within the bounds of the central collimating section 213, are generally not received and propagated by either of the collimating sections 210a and 210b because these gamma rays are outside of the corresponding fields of view of the collimating sections 210a, 210b. The optional collimator 204 of the upper detector-head 102U, which is similarly configured, also has a corresponding "dead" imaging zone. For A=B, the height H of the "dead" zone is defined by the width W of the central collimating portion 212 and the slant or inclination angle A via W=2H·tan A. For example, a central collimating section having a width of W=2.3 cm defines the height of the dead zone to be about H=2 cm.

The formation of the "dead" zone 224 due to slanting the holes or channels of the side collimating zones 210a, 201b with respect to those of the central collimating zone 212 and a corresponding increase in spatial resolution along the z-axis can be advantageously utilized to reduce the likelihood that a biopsy needle, inserted into the breast 220 from above, will penetrate through the lower side of the breast 220 and impact the collimator 204 of the lower detector head 102L. Accordingly, the risk of contaminating a biopsy needle with lead from the collimator and introducing these contaminants into the breast 220 is controlled. It is appreciated that an image, of a lesion 226 that is outside of the "dead" zone, formed by the collimator 204 of FIG. 2 includes three spatially-separate and localized in xy-plane image portions formed according to inclination angles A,B through respectively corresponding collimating sections 210a, 212, and 210b. Therefore, is a particular lesion is seen only at a portion of the image attributable to the central collimating section 212 of the collimator 204 and not at a portion of the image attributable to the collimating sections 210a, 210b, such lesion is located within the "dead" zone 224 of the collimator 204. A lesions within the "dead" zone of the collimator is considered to be located too closely to the lower detector head 102L for desirable biopsy. In this case, the breast 224 and the detector heads 102U, 102L can be mutually repositioned so that the lesion 226 is outside of the "dead" zone and, as a result, not in as close proximity to the lower detector head 102L.

Figure 3:
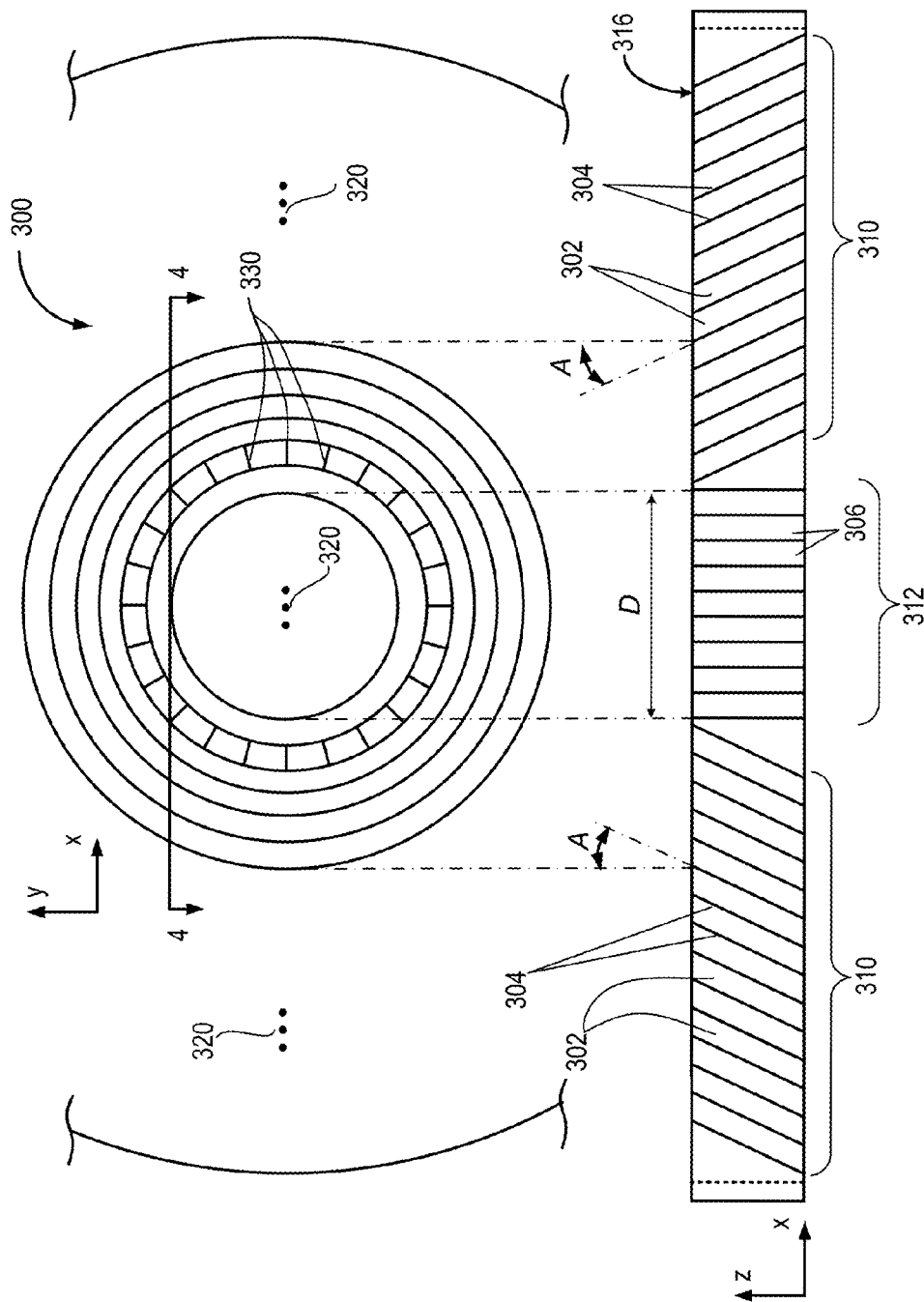
FIG. 3 is an elevational side view and associated top plan view of a conical slant-hole collimator in accordance with the present invention.

A related embodiment of a conical slant-hole collimator of the invention, discussed further in reference to FIGS. 3, 4A, 4B, and 5. FIG. 3 shows a portion of an embodiment 304 of the conical slant-hole collimator in both partial top plan view and a corresponding cross-sectional elevated view. The embodiment 300 includes a three-dimensionally (3D) varied geometry that is configured, as will be described, to gain localized spatial resolution along a direction of propagation of imaging gamma-rays (i.e., along the z-axis) as compared to a conventional, parallel-hole collimator. Moreover, the sensitivity of the embodiment 300 is also increased as compared to a conventional, parallel-hole collimator, because the number of holes of channels of the collimator 300 receiving imaging gamma-rays that have traversed the lesion 226 is larger than in the case of the parallel-hole collimator. In addition, the three-dimensionally (3D) variable geometry of an embodiment of a collimator of the present invention is adapted to facilitate the ability of the system to provide real-time (generally, under a minute) visualization of the position of both a lesion in question and a radiolabeled needle. This, in turn, enables a radiologist to carry out the biopsy procedure (insert a needle into the lesion) without the need to wait several minutes for the acquisition of a confirmatory image. In comparison with the embodiment 204 of FIG. 2, the collimator 300 also includes a plurality of collimating sections 310, 312 having differing characteristics. Specifically, it is contemplated that the differing characteristics of the plurality of collimating sections 310, 312 may include differing collimation angles. The collimating section 310 is configured to circumscribe the centrally located collimating section 312.

Specifically, the structure of the central collimating section 312 is generally similar to that of the central collimating section 212 of FIG. 2 in that the section 312 of FIG. 3 includes a plurality of directional holes or channels aligned in a mutually parallel fashion generally perpendicularly to a gamma-ray-collecting surface 316 of the collimator 300. The holes or channels 302 of the peripheral collimating section 310, on the other hand, are configured to be conically shaped and positioned in a co-axial fashion such as to form concentric circles when viewed from above the gamma-ray-collecting surface 316. In a cross-sectional plane that is perpendicular to the gamma-ray-collecting surface 316 and contains a diameter of any of these concentric circles, the holes or channels 302 are seen, therefore, to inclined or slanted at a generally acute angle A, as measured with respect to the normal to the gamma-ray collection plane 316 of the collimator 300. The ellipses 320 indicate portions of the collimator 300 not explicitly shown in the views of FIG. 3.

Configuring an embodiment of the invention to include the above-mentioned conical slant-hole collimator section 310 and a vertical-hole collimation section 312 encircled by the section 310 offers additional operational advantages. Specifically, in comparison with the embodiment 204 of the collimator of FIG. 2, and given equal inclination angles A in both embodiments, the embodiment 300 achieves a factor of 5 to 10 gain in sensitivity.

As best illustrated in FIGS. 3 and 4A, it is contemplated that in one embodiment, at least the holes or channels 302 of the first, peripheral collimating region 310 may be further divided by including septa 330. The septa 330 are oriented, for example, in a radial fashion and distributed along the annular holes 302. In one embodiment, the surfaces of the septa 330 are substantially perpendicular to the surfaces of the walls 304. While FIG. 3 illustrates the presence of the septa 330 only in one annulus of the first collimating region 310 for simplicity of the illustration, it is understood that septa may be generally formed in any hole or channel 302 at any position in the collimating section 310. Likewise, as illustrated in FIG. 4A, it is contemplated that the second, central collimating region 312 may also include at least one septum 336 disposed in at least one of the vertically-oriented holes of channels 306. Generally, the septa are configured to subdivide a given collimating hole or channel to which they belong into collimating sub-channels.

Figure 4B:
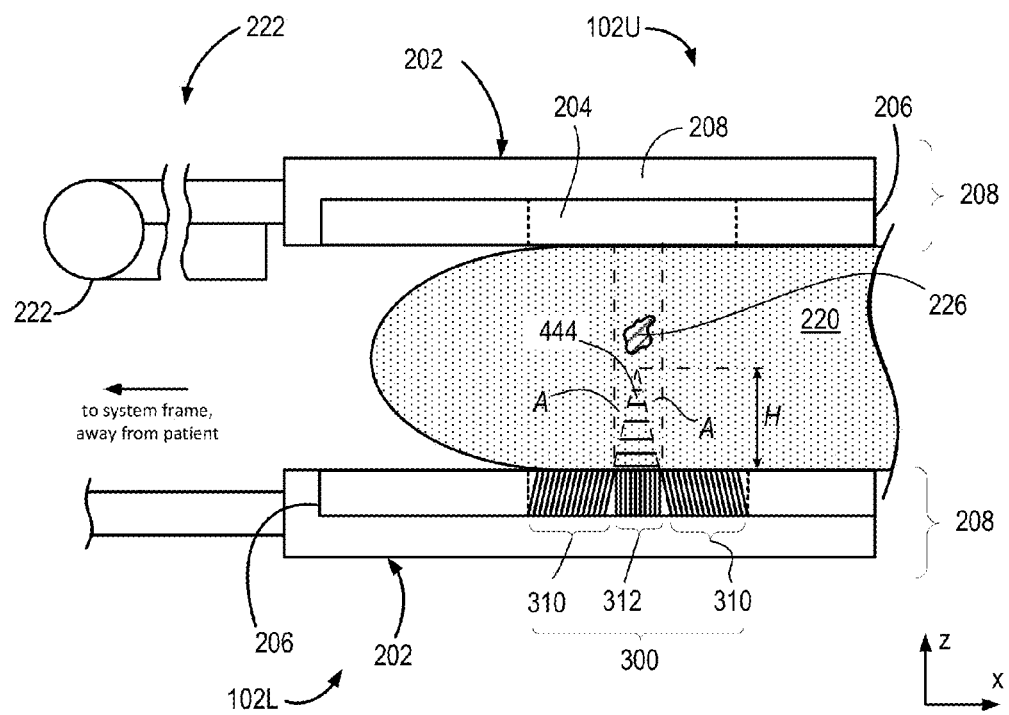
FIG. 4B is a side elevational illustration of the pair of opposed gamma detector heads of FIG. 1 showing a cross-sectional view of a conical slant-hole collimator of FIG. 3.

In further reference to FIG. 3 and referring to FIG. 4B, for imaging with the use of a conical slant-hole collimator, the breast 220 of a patient is positioned, again, between the detector heads 102U and 102L, at least one of which (for example, the head 102L) contains the collimator 300 in the collimator frame 206, and is lightly compressed therebetween. In a fashion similar to that described in reference to FIG. 2, a conical slant-hole collimator 300 also has a "dead" zone 444 associated with it. The "dead" zone 444 is substantially defined by a volume between the conical surface associated with the wall of the innermost hole 302 of the peripheral collimating section 310 and the gamma-ray collecting surface 316. A portion of the breast tissue located within such "dead" zone will be imaged substantially only by the central collimating section 312 and not by a peripheral collimating section 310.

Figure 5:
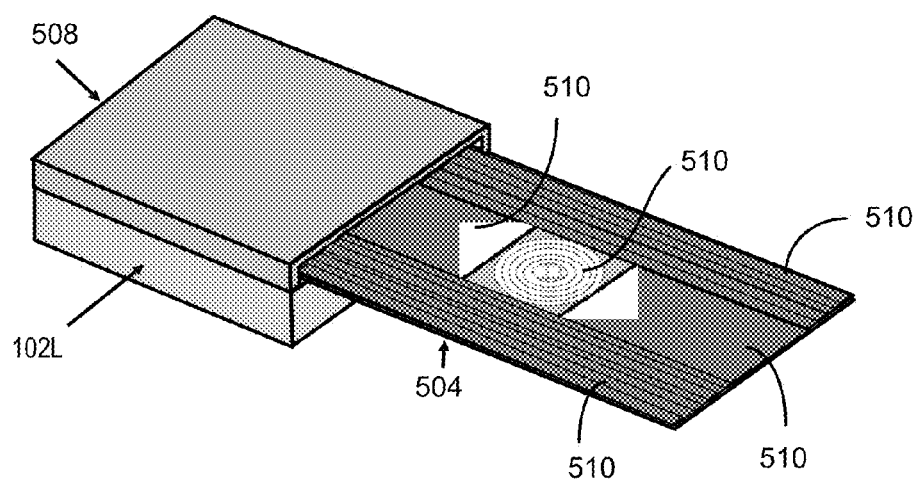
FIG. 5 is a perspective view of a system configured to repositioning of the conical slant-hole collimator of FIG. 3 in cooperation with a detector head according to the present invention.

In clinical use, the embodiment of the conical slant-hole collimator would be positioned directly underneath the lesion to be biopsied. FIG. 5 shows a portion 500 of the collimator repositioning system containing the embodiment 300 on a tray 504 that is configured to be slidable into a collimator sleeve 508. Lead plates 510 adjacent the collimator 300 on the tray 504 are positioned to limit the field-of-view of the detector (not shown) under the collimator 300 to that corresponding only to an area of the collimator 300. In use, the tray 504 is caused to slide into the sleeve 508 and is positioned beneath the lesion. For lesions located close to the chest wall (within approximately half the diameter of the conical collimator from the chest wall), a semi-circular version of the collimator (containing a left half of the collimator 300 as presented in FIG. 3) would be utilized to gain access to this part of the breast. While possessing only half the sensitivity of the full conical slant-hole collimator 300, the use of such half-conical slant-hole collimator will permit biopsy of lesions close to the chest wall.

Figure 6B:
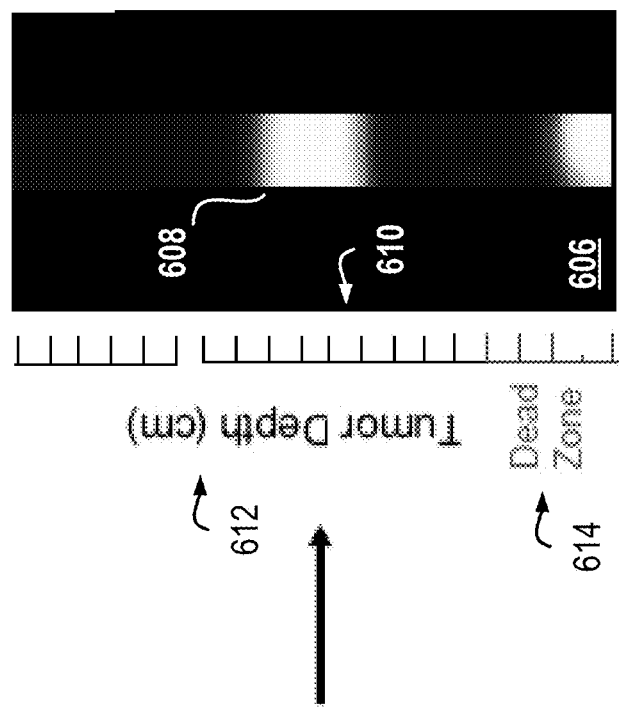
FIGS. 6A, 6B are examples of an image and an image-display configuration provided by the MBI and collimator systems of FIGS. 1, 3, 4A, and 4B.
Figure 6A:
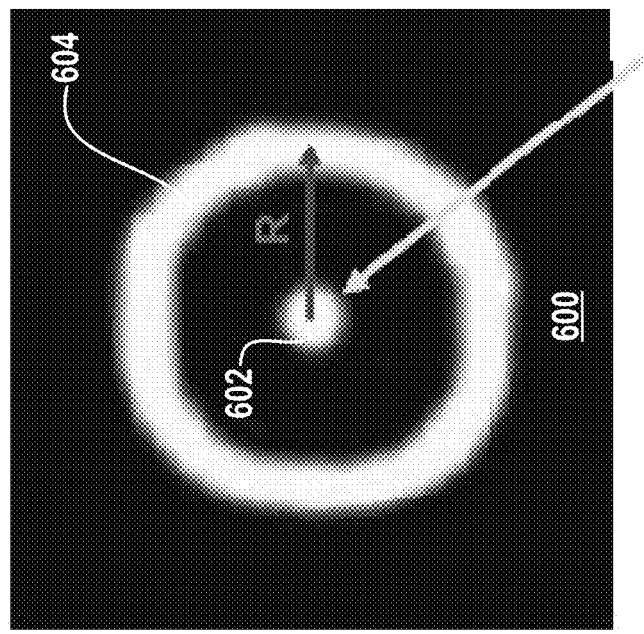

FIG. 6A shows an example of an image 600, of the lesion 226 located in the breast 220 outside of the "dead" zone of the collimator 300, that has been simulated with the use of the system of FIG. 4A. It is understood that the central collimating portion 312 of the collimator 300 is configured to deliver gamma-rays to a first, central area of the detector array 208, the peripheral collimating section 310 of the collimator is configured to deliver gamma-rays to a second area of the detector that circumscribes or is extended circumferentially, around the first area and that is separated from the central area of the detector by an annular region. Accordingly, a pattern of gamma-rays delivered by the collimator 300 to the detector array 208 includes two spatially-separate gamma-ray pattern portions, one of which encircles another. As a result, in the image 600, the lesion 226 appears as a combination of a "hot spot" image portion 602 and a "ring" image portion 604 encircling the "hot spot" portion 602. The "hot spot" 602 corresponds to imaging of the lesion 226 with the central, vertical-hole collimating section 312 of the collimator 300, and a "ring" image portion 604 corresponds to imaging of the lesion 226 with the peripheral, conical slant-hole collimating section 310 of the collimator 300. The depth of the lesion's location within the breast 220 can be calculated from the diameter (or radius) of the "ring" 504.

In order to view a lesion at a depth of 6 cm, for example, and assuming the collimation angle A=30°, the peripheral collimating section 310 of the collimator 300 would need to be approximately 6.9 cm in width (2×6 cm×tan 30°). A conical collimator configured according to the embodiment 300 of the invention would be about 7-9 cm in diameter.

Interpretation of an image such as the image 600 of FIG. 6A, may not be intuitive because the system employing the conical slant-hole collimator 300 may, in some cases, have a somewhat reduced spatial resolution in a plane of the detector (i.e., in an xy-plane) as compared with a conventional, parallel-hole collimator has holes or channels oriented substantially parallel to a direction of propagation of gamma-rays (i.e., along the z-axis), because a portion of gamma-rays that have traversed the lesion 226 are now directed to the detector by the conical section 310 and, therefore, give rise to image data representing axial position of the lesion 226 along the z-axis. Stated differently, the collimator 300 of the lower detector head 102L, because of its varied geometry, allows to counterituitively gain localized resolution of imaging in a third dimension along with the ability to provide real-time feedback at, possibly, some expense of the conventional resolution in only two dimensions afforded by a parallel-hole collimator. It is appreciated that the portions 602 and 604 of the image 600 both include image information about a local area, of the imaged breast 220, defined by the lesion 226 that is outside of the "dead" zone 444 of the collimator 300 and the surrounding tissue that is also outside of the "dead" zone 444. Such local area, therefore, is "spatially displaced" in the process of imaging in the image 600 to be reflected in both the hot spot 602 and the ring 604). Based on this realization, one can track a biopsy needle with a radio marker as the needle is guided from the top of the breast toward the tumor 224 by continuously updating the image 600 in real time and ensuring that the imaged needle remain centered on the "hot spot" 602 while moving inward from the "ring" 604 toward the "hot spot" 602. In this regard, localized spatial resolution is provided in a two-dimensional image 600 in three dimensions by way of the relative position of the needle with respect to the hot spot 602 (resolution in xy-plane) and with respect to the ring 604 (resolution along the z-axis).

In addition, by visualizing the data reflected in the image 600 differently, real-time feedback for interventional procedures can be readily achieved in another, highly-intuitive form. It is contemplated that a center of mass determination of activity about the hot spot 602 can be used during the biopsy process to verify that the lesion 226 has not shifted during biopsy due to patient motion or movement of the tumor within the breast during the biopsy process. Specifically, radial summation of the image intensity around the ring 604 is performed to convert the initial image 600 into a single vertical line image 606 of FIG. 6B. In this image 606, the ring 604 of FIG. 6A now appears as a single area 608 of increased activity on a vertical scale 610. The scale 610 is appropriately calibrated to indicate the depth of the lesion (or its separation) from the upper detector head or paddle 102U in area 612, and to indicate s the "dead" zone 444, where performance of needle biopsy is problematic, in area 614. In a related embodiment, the scale 610 could be appropriately inverted to indicate the depth of the lesion (or its separation) from the lower detector head 102L, if in the system of FIG. 4A the collimator 300 is engaged with the upper detector head 102U instead of being engaged with the lower detector head 102L.

Figure 7B:
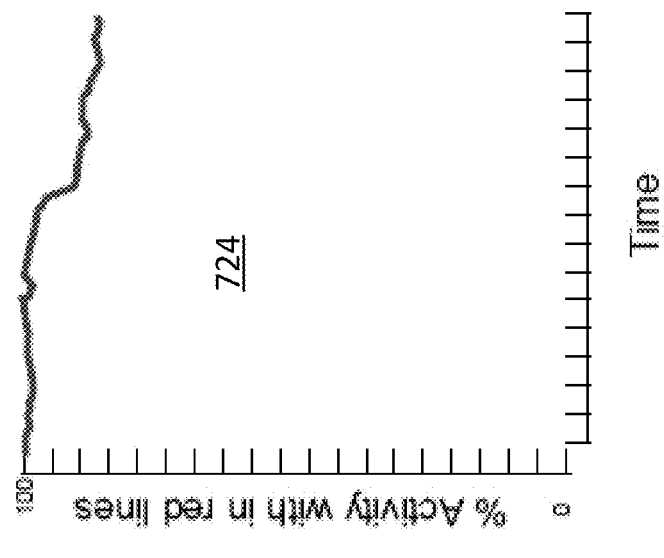
FIGS. 7A, 7B are views of alternative images and image-display configurations provided by of the MBI and collimator systems of FIGS. 1, 3, 4A, 4B configured to provide real-time biopsy guidance using the MBI system of FIG. 1.
Figure 7A:
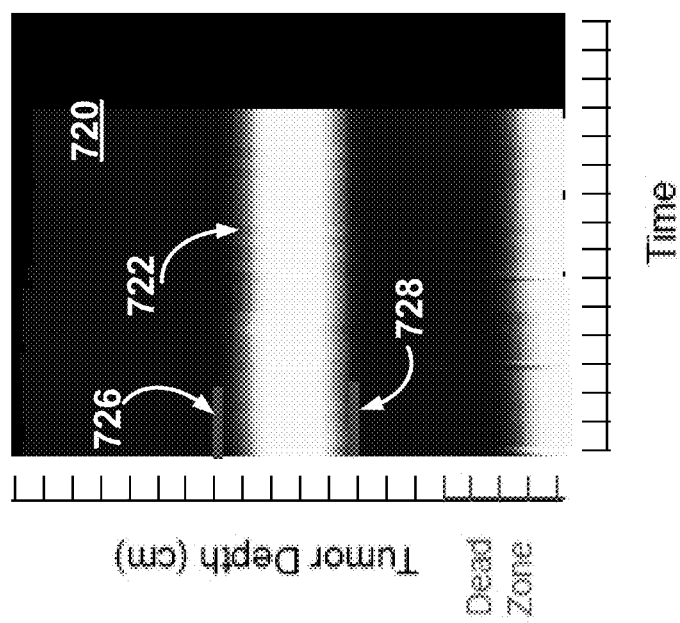

With the above-described configuration, when the acquired image is updated in real time, biopsies are performed with the data being acquired in a dynamic mode. Referring to FIG. 7A, at user-determined frame rate (typically every 5-15 seconds depending on type of activity), each image frame of the dynamic image acquisition is summed and displayed next to the previous image frame to form a series of images of consecutive image-frames. In this way, a time-series image 720 is provided that resembles an "ECG-type" display trace showing the location of the lesion 226 and any other radioactive source in the field of view of the conical collimator 300. Using this time-series image display scheme, any change in the quantitative estimate of lesion activity can be determined For example, changes in a portion of the image-trace 722 (such as its width or intensity, for example) are useful in determining if the biopsy process successfully removed any part of the imaged breast tumor. Within a tumor-related area defined by a pair of lines 726, 728 of the time-series image 720, the produced image information can be utilized in a number of ways. For example, measurement of the center of mass of activity of such area can be used to monitor a movement of the tumor. Summation of activity within the tumor-related area can be used to generate a display 724 of activity and, therefore, enable the user to distinguish a change in activity due to partial removal of the tumor rather than that due to a movement of the tumor outside the central field of view. For example, reduction in tumor activity with no change in the center of mass would be consistent with the tumor removal. In comparison, reduction in tumor activity accompanying a change in location of the center of mass would be consistent with movement of the tumor. This is an advantageous check, as it is possible for the patient to move, or for the lesion to be displaced by the needle during the biopsy process.

In addition, it is contemplated that the biopsy needle or other locator similar to the introducer in MRI biopsy systems, may contain an intense source of radioactivity at a lower energy than that emitted by the radiopharmaceutical located in the lesion (e.g. I-125 seed source, Tl-201 source). Accordingly, images of the needle would not interfere with images of the lesion, but could be processed in a similar manner and superimposed on the vertical trace image to provide the radiologist with real-time feedback on the location of both the lesion and the biopsy needle or locator.

The above-described embodiments of a system and method for real-time MBI guided biopsy of the breast also enable simultaneous MBI/ultrasound imaging of the breast tissue. This system provides a more complete imaging solution for women with dense breast tissue where the sensitivity of mammography is known to be limited, and does so in a cost-effective manner that permits its widespread adoption into clinical practice.

In a conventional configuration, imaging information is typically obtained sequentially from the two imaging modalities and some motion or movement of the breast between the two imaging processes may occur. However, the proposed configuration is beneficial in that the location of a lesion that is not visible on a conventional ultrasound image can be determined and indicated on a MBI image, and may also be identifiable from enhanced ultrasonic techniques, such as elastography, thereby permitting ultrasound-guided biopsies if desired. In practice, in a high percentage of cases (for example, greater than eighty percent), a lesion can be seen on just the lower MBI detector; thus, during ultrasound imaging, information on the location of the lesion can be updated on the ultrasound system to confirm that the location of a lesion has not shifted in the conversion from MBI to ultrasound imaging modes.

Referring again to FIGS. 1, 2 and 4B, imaging of the breast 220 is performed using the aforementioned MBI system embodiment 100 of FIG. 1 that includes, in relevant part, a set-up of FIG. 4A. The results of such imaging which permit a calculation of an in-plane (x and y) location of a lesion in the breast 220 as well as its depth (relative position along the z-axis), and relative uptake of an administered radionuclide. In one embodiment, As illustrated in FIG. 4B and further described below in reference to FIGS. 8 and 9, the upper detector head 102U may be affixed to a rotatable gantry arm, which provides a rotation of the upper detector head 102U (for example, in the xz-plane, about a hinge 222) and facilitates interchangeability of the upper detector head 102U with other functional components devices, such as an ultrasound system, for example.

Figure 8:
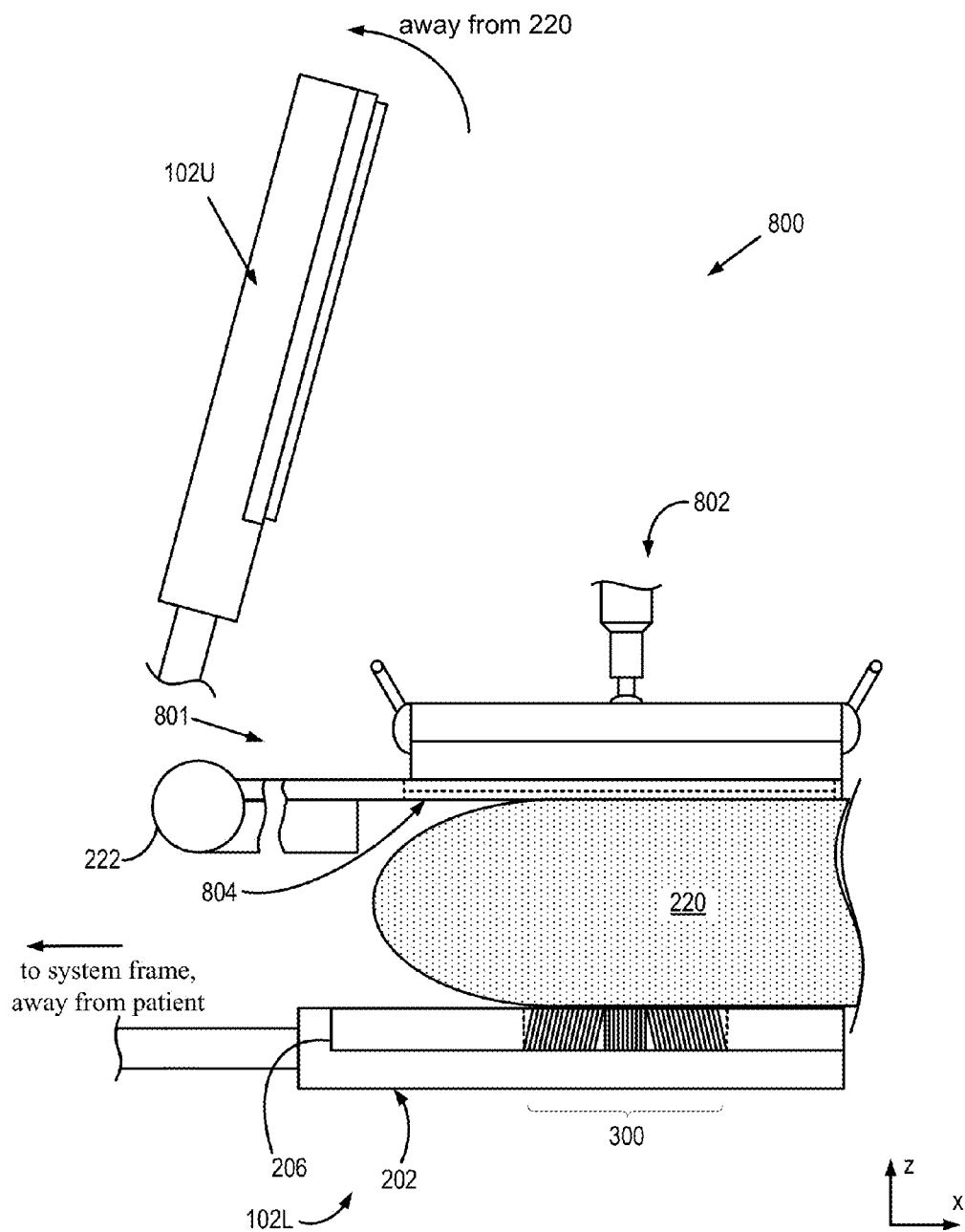
FIG. 8 is a side elevational view of a reconfigurable system in which a gamma detector head is replaceable by an ultrasound system.

In particular, FIG. 8 shows a reconfigurable embodiment 800 of the invention configured to facilitate imaging of breast tissue with multiple modalities. As shown, the upper detector head 102U is adapted to be disengageable from the remaining portion of the MBI system to be replaced by another system such as, for example, an ultrasound system 801 that, for example, may include a WUS sub-system 802 having an ultrasound paddle dimensioned similarly to the upper detector head 102U. An acoustic coupling plate 804 of the US system 801 is designed to provide a contact surface for receiving and compressing a portion of a subject under examination (such as a portion of the subject's breast 220). In the described reconfigurable embodiment 800 of the MBI/WUS system, the WUS sub-system 802 acts as one part of a compression device to lightly compress breast 220 between the WUS system 802 and the lower MBI detector head 102L. The acoustic coupling plate 804 is composed of a material with low acoustic attenuation, and is preferably composed of a material with ultrasonic reflective properties that are similar to those of a soft tissue. Examples of appropriate materials include nylon and latex. The acoustic coupling plate 804 is adapted so as to permit the passage of a biopsy needle through the acoustic coupling plate 804 and into the breast 220. For example, a nylon mesh can be employed and manufactured with a grid of holes to allow a needle to be passed through for breast biopsy. Additionally or in addition, the acoustic coupling plate 804 is adapted to retain the breast 220 in a compressed position prior to retraction of the upper detector head 102U.

Examples of WUS sub-systems that can be used with embodiments of the invention include a combined ultrasound probe and compression paddle device marketed under the trademark SomoVu™ (U-Systems, Sunnyvale, Calif.). The WUS sub-system 802 is normally designed to be placed directly on the breast tissue with the patient supine. The operator can then perform an automated scan of the breast.

In addition or alternatively, it is contemplated that an embodiment of the reconfigurable MBI-ultrasound system such as the embodiment 800 possesses the capability for elastography on the ultrasound system. Examples of usable systems include an ultrasound probe with elastography capability marketed under the trademark Aixplorer™ (SuperSonic Imagine, Aix-en-Provence, France). The Aixplorer is normally designed to be placed directly on the breast tissue with the patient supine. In the described configuration 800 of FIG. 8, the Aixplorer probe (not shown) is placed on top of the acoustic coupling plate 804, and shearwave elastography is performed over the region of abnormal uptake identified in the MBI images.

In operation, and in further reference to FIG. 8, the patient is seated and the breast is lightly compressed by the WUS system 802 and lower MBI detector head 102L, in the orientation similar to that of the mammography procedure. Functional imaging of the breast is performed using the MBI system (for example, with the conical slant-hole collimator 300) and, simultaneously or sequentially, the WUS system 802 is operated to complete a sweep across the breast 220 to obtain 3D images of the breast tissue. Upon completion of both image acquisitions, the MBI and WUS images may be co-registered. Advantages of the proposed embodiment include reduced scan time due to the simultaneous acquisition of both the MBI and WUS images, and reduced likelihood of motion artifact causing misregistration. In addition, when using the systems described above with respect to FIGS. 3, 4A, 4B, 5, 6A, 6B, 7A, 7B, the configuration of FIG. 8 can also provide depth-resolved information about the location of a lesion.

Figure 9A:
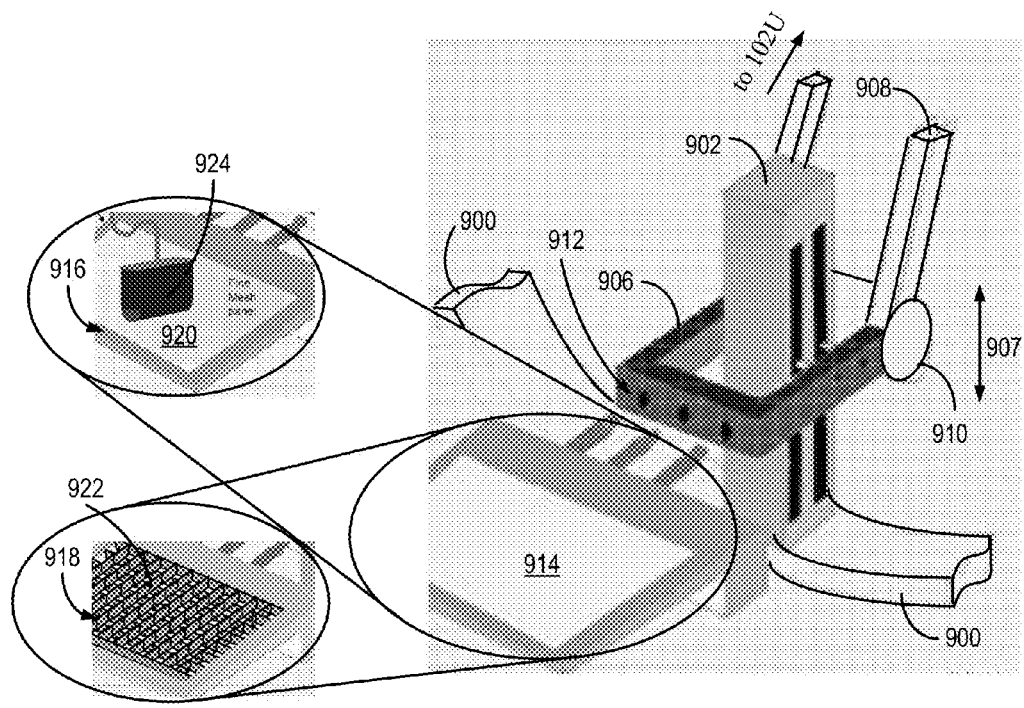
FIG. 9A is a perspective view of an alternative configuration, including a gantry-based support system, for use with the systems of FIGS. 1-8.
Figure 9B:
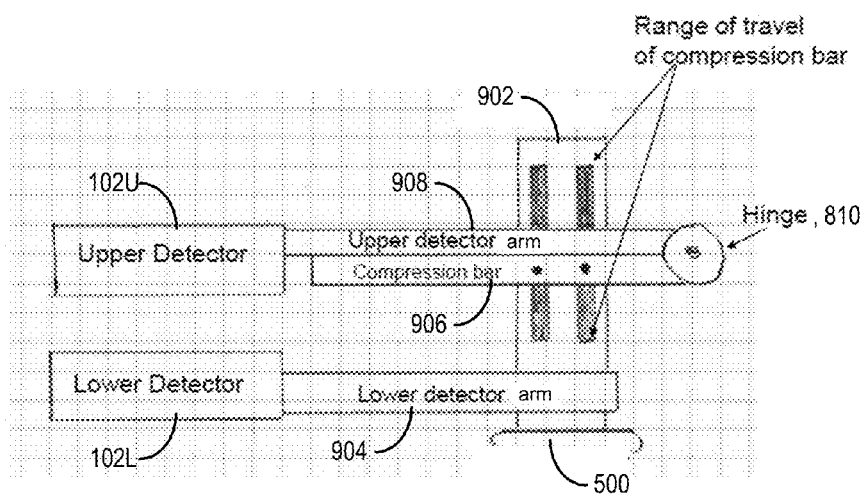
FIG. 9B is a side, elevational view of the gantry-based support system of FIG. 9A.

Referring to FIGS. 9A and 9B, the examples of structural details of the above-referenced embodiment 800 of a reconfigurable MBI/WUS system are discussed. The embodiment 800 may be mechanically articulated, as shown, with a gantry 900, such as that identified as a "Giotto gantry" and available from IMS of Bologna, Italy. A central column 902 is mounted on the gantry 900. Extending from the central column 902 is a lower supporting arm (or lower detector arm) 904 that, in the illustrated configuration, holds the lower detector head 102L in a fixed position. Another, intermediate arm includes a compression bar 906 connected to the central column 902 and to an internal motor (not shown) that drives and repositions the compression bar 906 along central column 902, as shown schematically with an arrow 907. Yet another upper supporting arm (or upper detector arm) 908 is pivotally connected, at its proximal end, to the intermediate arm (compression bar 906) through a hinge 910. Opposite the hinge 910, the upper supporting arm 908 is engaged at its distal end with the upper detector head 102U, as described above.

FIG. 9A shows the embodiment of the system with the upper arm 908 and the compression bar 906 in an open position, when the upper arm 908 is pivoted away from the compression bar 906 such that the upper detector head 102U is out of view and out of operable communication with the breast tissue. In comparison, FIG. 9B shows the embodiment with the upper supporting arm 908 and the compression bar 906 in a closed, mutually adjoining position, when the upper supporting arm 908 and the compression bar 906 are engaged and, optionally, locked together to achieve proper breast compression with the upper detector head 102U. The hinge 910 may be spring-loaded so that some user-applied compressing force is needed to engage the upper detector arm 908 to the compression bar 906. Such loading reduces the likelihood of the upper supporting arm 908 being dropped too abruptly onto the compression bar 906, as the spring absorbs some of the weight of the upper detector head 102U and upper detector arm 808. As mentioned above, the movement of the compression bar 906 along the central column 902 is used to compress the breast tissue between the upper and lower detector heads 102U, 102L.

The open position and/or orientation between the upper arm 980 and the compression bar 906 of the orientation in which an embodiment of the system may be utilized for both combined MBI/ultrasound imaging and for MBI-guided breast biopsy. In one embodiment, for example, the compression bar 906 is adapted to removably receive at least one auxiliary component. To this end, the compression bar 906 is equipped with several locating holes 912 configured to receive an attachable device such as a new compression paddle or device 914. For example, the acoustic coupling plate 804 described above in reference to FIG. 8, or other functional components could be removably engaged with the compression bar 906 via the locating holes 912.

For example, as further shown in FIG. 9A, two types of paddles 916, 918 are contemplated for use with the compression bar 906. The first paddle 916 includes a central section covered with a thin acoustically-transparent mesh 920. When the paddle 916 is cooperated, as a device 914, with the compression bar 906 and the breast tissue (not shown) is compressed between the detector head 102L and the paddle 916, an ultrasound probe 924 can be acoustically coupled to the compressed breast tissue through the mesh 920. The precise location of a lesion derived from the image registered, as described above, with the MBI detector head 102L can be used to properly position the ultrasonic probe 924 with respect to the mesh panel 920 and to permit co-registration of the MBI and ultrasonic images. In one implementation, for example, such positioning of the ultrasonic probe 924 can be achieved by marking the mesh 920 with a grid pattern appropriately labeled to match locations on the MBI images. The coordinates of the lesion location on the MBI image can then be used to determine the appropriate co-registered position of the ultrasound probe 924 on the mesh 820. In another implementation, the location of the lesion on the MBI image may be electronically entered into the ultrasound system and an electronic mark on the ultrasound image may be further used to direct the positioning of the probe 924 with respect to the mesh 920 and to confirm co-registration of the MBI and ultrasound information.

Another paddle 918, for use as the attachable device 914 with the compression plate 906, includes a central section formed of a set of guide holes 922 appropriately configured for biopsy procedures. Here, again, the location on the MBI image can be used to determine the location for the biopsy needle to be placed through the guide holes 922. Real-time imaging, such as described above, may be used to determine depth information and track the location of a lesion, which may shift during the biopsy process.

Figure 10A:
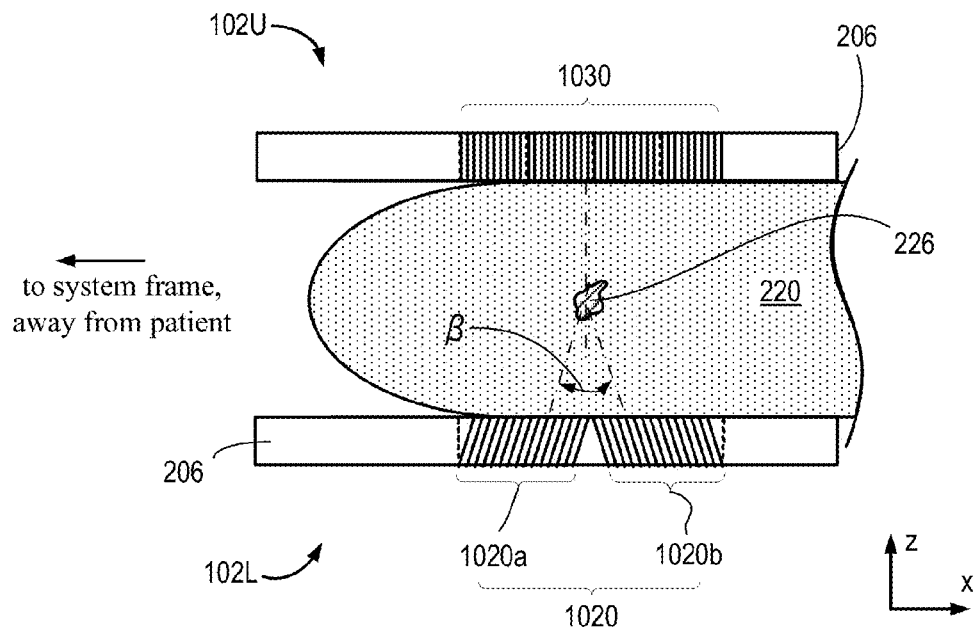
FIG. 10A is a diagram depicting a tumor located centrally in the breast and imaged with the use of both sections of a conventional slant-hole collimator
Figure 10B:
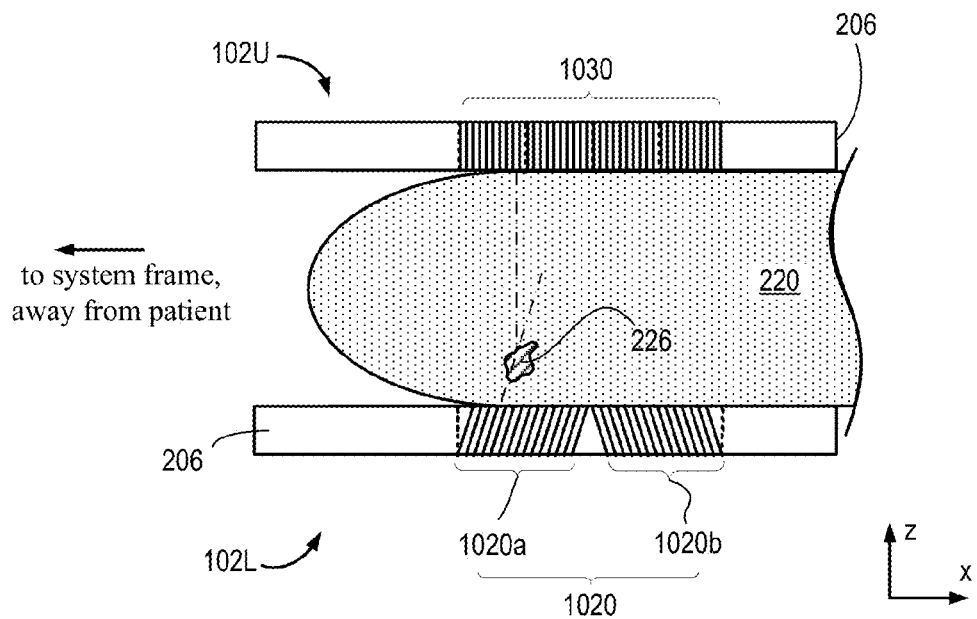
FIG. 10B is a diagram depicting a tumor located in a lower portion of the breast such that imaging is carried out with only one section of a conventional slant-hole collimator.

Referring now to FIGS. 10A, 10B, side elevational views are shown of a portion 1010 of an imaging system including conventional bi-focal slant-hole collimator that contains a lower portion 1020 (with stationary slant-hole sections 1020a, 1020b) in the collimator frame 206 of the lower arm 102L and an upper portion (with a stationary straight-hole collimator section 1030) in the collimator frame 206 of the upper arm 102U. Each collimating hole or channel of the section 1020a forms the same angle β with respect to any of holes or channels of the section 1020b. FIG. 10A illustrates a situation when the tumor 226 being imaged is located substantially in the central portion of the tissue 220. In comparison, FIG. 10B shows the situation when the tumor is in the lower portion of breast tissue that is closer to the lower portion 1020 of the collimator and can be imaged only by one of the slant-hole collimating sections (the section 1020a, as shown) during the imaging procedure.

It is readily understood that in the latter situation and, more generally, in a situation when the tumor is far away from the straight-hole collimating section 1030, imaging data acquired by the straight-hole section 1030 may not be completely reliable as the tumor 226 may not be well imaged with the straight-hole section 1030. For example, the diagram depicted in FIG. 10A shows that all three sections of the collimator (sections 1020a, 1020b, and 1030) provide imaging data based on which the information about the depth coordinate (i.e., position along the z-axis) of the tumor 226 can be devised. In contradistinction, the diagram depicted in FIG. 10B shows that, at best, only 2 collimating sections (sections 1020a and 1030) participate in imaging of the tumor 226 because the tumor 226 is located outside of the FOV of the section 1020b. In addition, because the tumor 226 is far away from the upper collimating section 1030 (as shown, at the lower portion of the breast 220), the imaging data acquired by the straight-hole collimating section 1030 may not be reliable and, therefore, there may exist substantially only one set of reference data (i.e., the imaging data acquired by imaging through the collimating section 1020a) based on which the depth coordinate of the tumor can be determined Consequently, in the latter case, triangulation of the position of the tumor 226 and determination of its depth coordinate remain problematic.

Figure 11A:
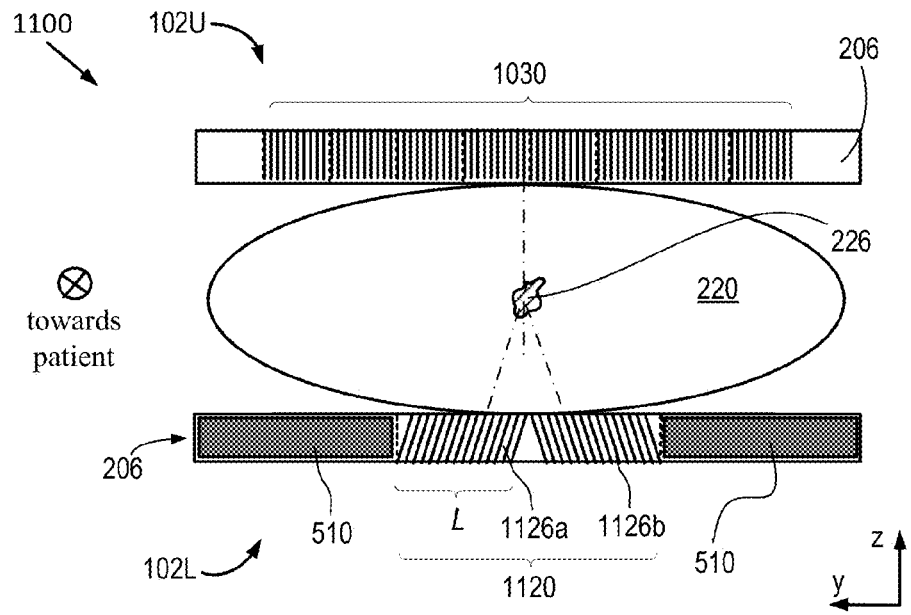
FIGS. 11A and 11B are diagrams showing an implementation of the slant-hole collimator according to the present invention configured to image a tumor in different locations across the breast tissue.
Figure 11B:
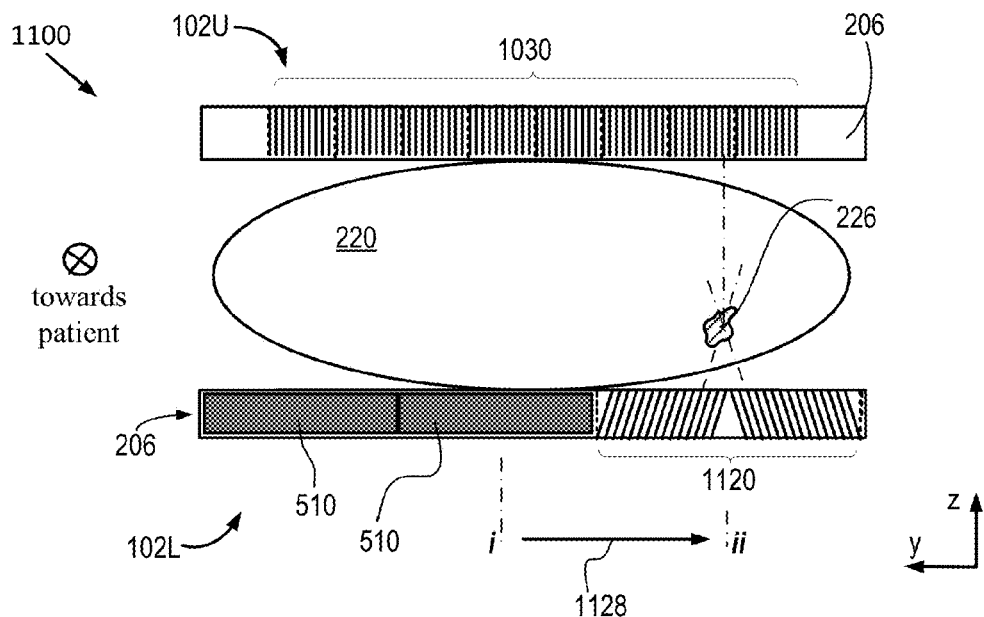

An embodiment 1100 of the multi-segmented collimator shown in FIGS. 11A, 11B solves this problem by providing a collimator that includes multiple collimating sections that are repositionable with respect to the tissue and/or tumor being imaged. In addition, the multiple collimating sections may be configured such as to provide a collimator imaging the tumor at multiple spatial angles and, therefore, having multiple collimation characteristics, for example multiple foci.

In particular, FIGS. 11A and 11B show, in front elevated view and not to scale, the embodiment 1100 that includes a lower portion 1120 of the collimator containing slanted-hole sections and the upper straight-hole section 1030 of the collimator. In comparison with FIG. 10A, the diagram of FIG. 11A illustrates the situation when the slant-hole collimating sections 1120a, 1120b are disposed in a central portion of the frame 206 of the lower arm 102L and the tumor 226 is located in an area of breast tissue 220 that is imageable by all collimating sections (such as, for example, substantially in a central portion of the breast 220). In comparison with FIG. 10B, the diagram of FIG. 11B depicts a situation when the tumor 226 is located at a side of the breast tissue 220 and, consequently, would be outside of the FOV of at least one lower slant-hole section of the conventional collimator the slant-hole sections of which are stationary.

Figure 11C:
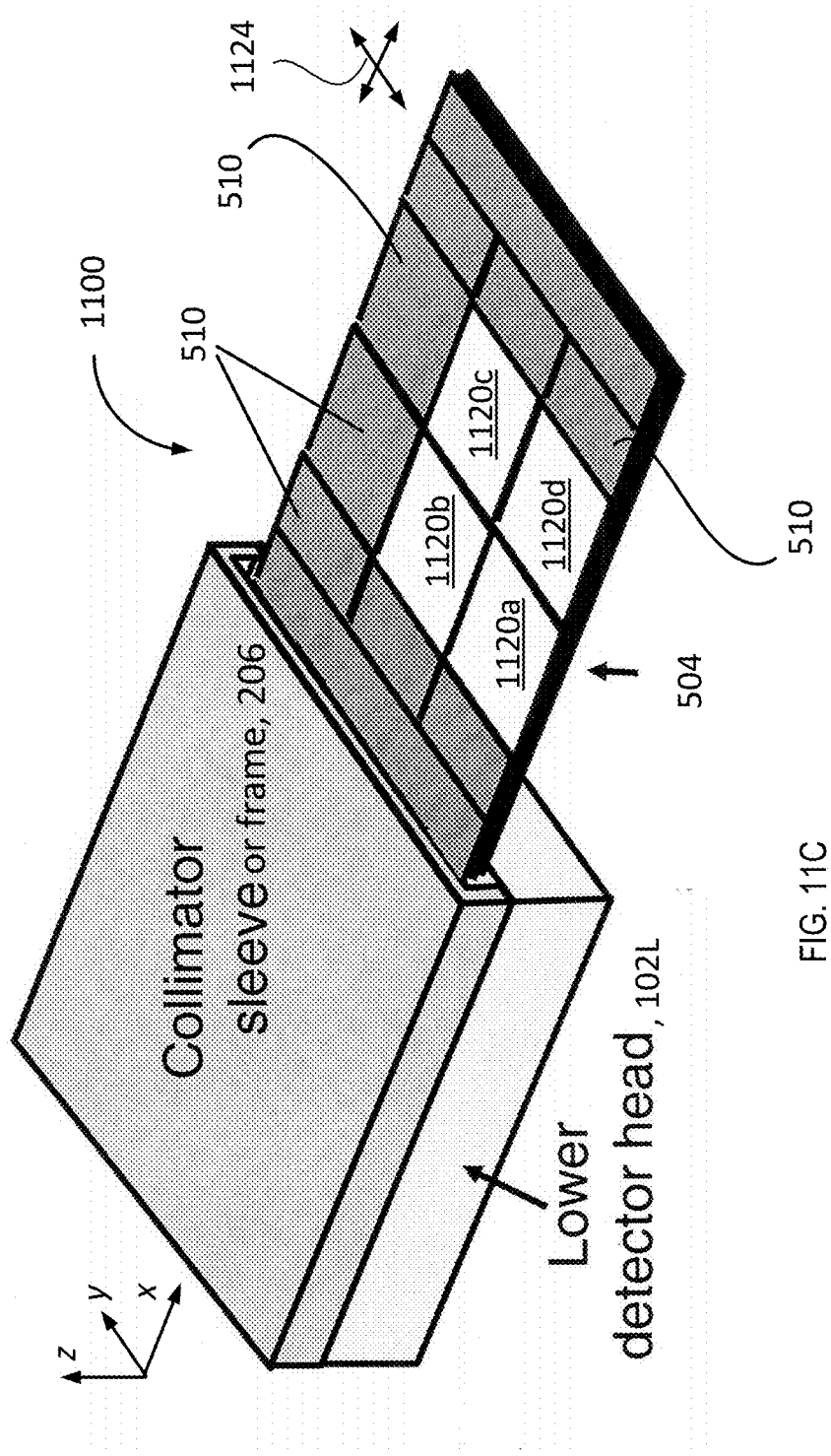
FIG. 11C is a perspective view of the collimator in a moveable tray slidable into a sleeve of the supporting arm of the MBI system.

Referring again to FIGS. 11A, 11B and in reference to FIG. 11C, a lower portion of the collimator is configured to include multiple collimating segments such as segments 1120a, 1120b, 1120c, and 1120d, each of which corresponds to a separate, independently repositionable and movable, within the tray 504, collimating section containing slanted holes or channels. The tray 504 is configured to be moveable within the sleeve or frame 206 in at least one direction, as indicated by arrows 1124. For example, the tray 504 is adapted to shift, by a predetermined amount d along the y-axis within the bounds of the sleeve 206 and, in addition or alternatively, to slide along the x-axis in and out of the sleeve 206. Such configuration ensures that the collimator is configurable such as to have the respective fields of view of at least two different collimating sections cover the region of interest where the tumor 226 is located. Generally, the collimator sleeve 206 is adapted to accommodate the transverse shift d, of the collimator tray 504, of about half the lateral extent of an individual collimating section such as the section 1120a.

Figure 12A:
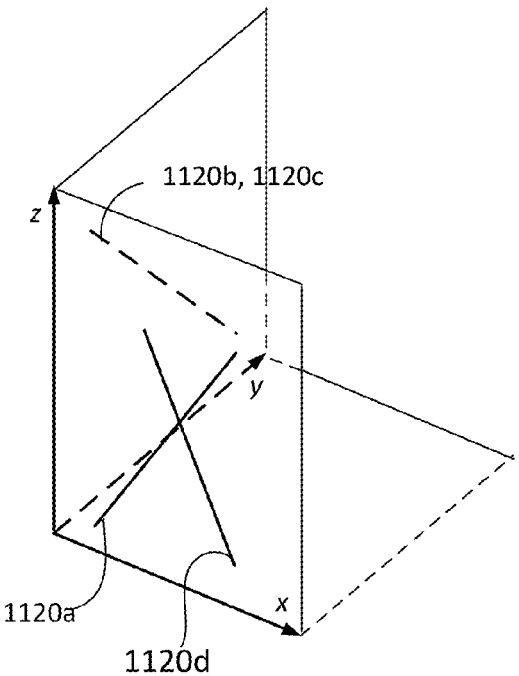
FIGS. 12A and 12B are diagrams showing two examples of different orientations of slant-holes of the collimator of the invention.
Figure 12B:
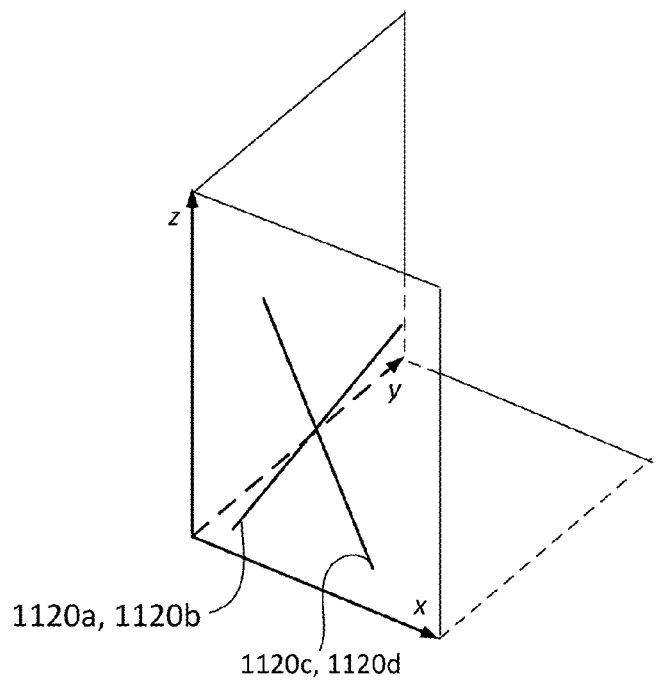

Each of the collimating segments or sections of the embodiment 1100 is configured to be appropriately matched to and in radiant communication with a pixilated detector (not shown) that adjoins the collimator in a known fashion. In one example, for a detector having an overall size of about 20×15 $cm^2$, the multisegmented collimator includes four substantially square segments or sections, as shown in FIG. 11C, each of which is sized to about 5×5 $cm^2$. Each of the collimating sections 1120a, 1120b, 1120c, and 1120d can be oriented, at the immediate location of such section in the tray 504, such as to have the slanted holes or channels of the collimating section inclined in either of four directions (as shown, +x, −x, +y, −y) with respect to the z-axis. Accordingly, in the example of FIG. 11C, the multisegmented collimator 1120 may be configured to have multiple collimating angles (generally, up to four collimating angles). A diagrammatic example of the orientation of the slant holes or channels of the four individual collimating sections 1120a, 1120b, 1120c, and 1120d that provides for respectively corresponding three different collimation angles is shown in FIG. 12A. Another diagrammatic example, demonstrating the orientation of the slant holes ensuring two different collimation angles is shown in FIG. 12B. It is appreciated that, as a result of individual collimating section having different collimation characteristics, an image of the tumor 226 generally includes spatially separate image regions.

Referring again to FIGS. 11A through 11C, a portion of the tray 504 that is not occupied by the individual collimating sections 1120a through 1120d is covered with lead plates 510 adapted to substantially block the radiation (for example, gamma rays) from penetrating through the plates towards the detector and thereby blocking the imaging radiation in areas not corresponding to the collimating sections.

While the embodiment 1100 is shown to include four square collimating sections 1120a through 1120d, generally a number of the sections and their geometry does not affect the scope of the invention. For example, a slant-hole collimating section of a related embodiment may be shaped as a non-square rectangle, and the embodiment may contain an arbitrary number (for example, 2, 3, 5, or 6) of collimating sections. Moreover, in a related embodiment individual collimating sections may be positioned such as to be spatially separated in the tray 504 with interposing lead plate(s) 510 of predetermined width(s). Moreover, it is appreciated that at least one of the collimating sections such as sections 1120a through 1120d of FIG. 11C may include at least a portion of a conical slant-hole collimator such as that described in reference to FIGS. 3, 4A, 4B, 5. For example, in a configuration depicted in FIG. 11C, one of the "quadrants" 1120 through 1120d of the collimator of the invention can include either a whole conical slant-whole collimator 300 or one of its quadrants.

In further reference to FIG. 11B, the embodiment 1100 is configured to be easily adaptable to imaging a tumor 226 regardless of spatial position or orientation of the tumor 226 with respect to the spatial extent of the tray 504 and/or supporting arm 102L. Specifically, when the tumor 226 is at a side of the breast 220, section(s) of the multisegmented collimator are appropriately shifted or repositioned within the tray 504 from their initial, central position labeled as i to their alternate position labeled as ii, as shown by an arrow 1128. Such repositioning is carried out to ensure that the tumor is within the FOV of at least two individual slant-hole collimating sections having different collimating angles (as shown, sections 1120a and 1120b).

The present invention has been described in terms of one or more preferred embodiments, and it should be appreciated that many equivalents, alternatives, variations, and modifications, aside from those expressly stated, are possible and within the scope of the invention.

What is claimed is:

1. A molecular breast imaging (MBI) system comprising:
   an upper compression pad; and
   a lower compression pad including
      a lower gamma-ray detector and
      a lower collimator unit configured to deliver gamma-rays from a region of interest (ROI) between the lower and upper compression pads, the lower collimator unit including:
         a collimator tray; and
         multiple collimating sections that, when simultaneously disposed within said collimator tray, are individually repositionable within said tray with respect to one another based on an estimate of location of a tumor in the ROI such as to define at least one of i) different collimating angles and ii) different orientations for different collimating sections,
      wherein said multiple collimating sections include a first collimating section having a first collimation angle of said first collimating section,
         said first collimation angle of the first collimating section being defined between a first axis of the first collimating section and a normal to a surface of the lower compression pad,
         the first axis of the first collimating section being an axis of a first collimating channel of said first collimating section,
         said first collimation angle of the first collimating section being non-zero.

2. An MBI system according to claim 1,
   wherein the lower compression pad further includes a collimator sleeve having an inner volume that is dimensioned to slidably accept therein said collimator tray with said multiple collimating sections disposed within the tray, and
   wherein said multiple collimating sections of the lower collimator unit further include
      a second collimating section having a first collimation angle defined between a first axis of the second collimating section and the normal,
      said first axis of the second collimating section defined between an axis of a first collimating channel of the second collimating section,
      the first collimation angle of the second collimating section being non-zero,
   wherein each of said first and second collimating sections is repositionable within said tray such as to define first and second planes that are perpendicular to one another,
      the first plane being a plane defined by the normal and the first axis of the first collimating section;
      the second plane being a plane defined by the normal and the first axis of the second collimating section.

3. An MBI system according to claim 1, further comprising at least one of a disengageable acoustic coupling element, adapted to receive an ultrasound imaging apparatus, and a disengageable biopsy element, adapted to receive and pass a biopsy needle therethrough towards the collimator.

4. An MBI system according to claim 1, wherein the upper compression pad includes an upper collimator and an upper gamma-ray detector configured to receive gamma-rays from a portion of a subject arranged between the upper and lower collimators.

5. An MBI system according to claim 4,
   wherein the multiple collimating sections include a first collimating section with linearly configured slant-holes includes with respect to an axis that is normal to a surface of the first collimating section, and
   wherein the upper collimator contain slant-holes that are substantially parallel to an axis that is normal to a surface of the upper collimator.

6. An MBI system according to claim 4, further comprising a gantry system supporting the upper and lower compression pads to permit relative motion of said pads about the gantry system.

7. An MBI system according to claim 1, further comprising a biopsy element configured to engage with the MBI system such as to receive and pass a biopsy needle therethrough toward the lower compression pad.

8. An MBI system according to claim 1, wherein each of the multiple collimating sections has a corresponding focus, and wherein foci of the multiple collimating sections differ from one another.

9. An MBI system according to claim 1, wherein said first collimating section further has a second collimation angle,
   said second collimation angle of the first collimating section defined between a second axis of the first collimating section and the normal,
   the second axis of the first collimating section being an axis of a second collimating channel of said first collimating section,
   said second collimation angle of the first collimating section being non-zero.

10. An MBI system according to claim 9, wherein said first collimating section further has a third collimation angle,
   said third collimation angle of the first collimating section defined between a third axis of the first collimating section and the normal,
   the second axis of the first collimating section being an axis of a third collimating channel of said first collimating section,
   said third collimation angle being zero.

11. An MBI system according to claim 10, wherein said first collimating section is structured such that a portion of said ROI that is within a field-of-view (FOV) corresponding to the third collimation angle is not covered by either a FOV corresponding to the first collimation angle or a FOV corresponding to the second collimation angle.

12. An MBI system according to claim 9, wherein said first collimating section defines conical collimation.

13. A method for performing an image-guided biopsy of a tissue, the method comprising:
positioning a portion of the tissue to be imaged between first and second compression members,
wherein the first compression member includes a first gamma-ray detector in operable communication with a first collimator unit that contains
a collimator tray; and
multiple collimating sections that, when simultaneously disposed within said collimator tray, are individually repositionable within said tray with respect to one another based on an estimate of location of a tumor in the ROI such as to define at least one of i) different collimating angles and ii) different orientations for different collimating sections,
initiating a biopsy procedure on the portion of tissue through one of said compression members;
displaying an image of the portion of the tissue based on information acquired by the gamma-ray detector about gamma rays that have passed through said multiple collimation sections; and
processing imaging data representing a status of the biopsy procedure.

14. A method according to claim 13, wherein displaying an image includes displaying an image representing a common, substantially spatially-overlapping area in the portion of the tissue that is spatially displaced in the image.

15. A method according to claim 13, wherein processing imaging data includes processing imaging data representing a location of a biopsy needle with respect to at least one of the first and second compression members.

16. A method according to claim 13, further comprising receiving ultrasound imaging data from an acoustic coupling element coordinated with the second compression member opposite the collimator.

17. A method according to claim 13, wherein positioning includes positioning a portion of the tissue being imaged in proximity to a compression member that is configured to receive a re-attachable device.

18. A method according to claim 13, further comprising determining parameters of spatial location of a biopsy needle within the tissue, said parameters including a depth value derived from geometry of said displayed image.

* * * * *